(12) United States Patent
Potyrailo et al.

(10) Patent No.: US 9,678,030 B2
(45) Date of Patent: Jun. 13, 2017

(54) MATERIALS AND SENSORS FOR DETECTING GASEOUS AGENTS

(71) Applicant: General Electric Company, Schenectady, NY (US)

(72) Inventors: Radislav Alexandrovich Potyrailo, Niskayuna, NY (US); Zhexiong Tang, Niskayuna, NY (US); Brandon Bartling, Woodbury, MN (US); Nandini Nagraj, Clifton Park, NY (US); Vadim Bromberg, Niskayuna, NY (US)

(73) Assignee: General Electricity Company, Schenectady, NY (US)

( * ) Notice: Subject to any disclaimer, the term of this patent is extended or adjusted under 35 U.S.C. 154(b) by 151 days.

(21) Appl. No.: 14/586,485

(22) Filed: Dec. 30, 2014

(65) Prior Publication Data

US 2016/0187280 A1 Jun. 30, 2016

(51) Int. Cl.
*G01R 25/00* (2006.01)
*G01N 27/22* (2006.01)
*G01N 33/00* (2006.01)
*G01N 31/10* (2006.01)
*G01N 27/12* (2006.01)

(52) U.S. Cl.
CPC .......... *G01N 27/228* (2013.01); *G01N 27/125* (2013.01); *G01N 27/227* (2013.01); *G01N 31/10* (2013.01); *G01N 33/0036* (2013.01)

(58) Field of Classification Search
CPC .. G01R 35/005; G01R 27/2605; G01R 35/00; G01R 27/28; G01R 27/02; G01R 27/2611; G01R 15/18; G01R 27/04; G01R 15/16; G01R 29/0807; G01R 29/18; G01R 31/027; G01R 31/2822; G01R 31/2837; G01R 31/2839
USPC ....... 324/652, 601, 675, 315, 633, 636, 655, 324/668, 682, 708
See application file for complete search history.

(56) References Cited

U.S. PATENT DOCUMENTS 7,911,345 B2 3/2011 Potyrailo et al.
8,364,419 B2 1/2013 Potyrailo et al.
(Continued)

FOREIGN PATENT DOCUMENTS

WO 2008041983 A2 4/2008

OTHER PUBLICATIONS

Ishihara et al., "Improved Sensitivity of CuO-BaTiO3 Capacitive-Type CO 2 Sensor by Additives", Sensors and Actuators B 28, Jul. 1995, vol. 28, Issue 1, pp. 49-54.

(Continued)

*Primary Examiner* — Patrick Assouad
*Assistant Examiner* — Taqi Nasir
(74) *Attorney, Agent, or Firm* — Jean K. Testa; Fletcher Yoder, P.C.

(57) ABSTRACT

A sensor for detecting gaseous agents has a transducer, which includes an electrical resonant circuit that forms an antenna. The sensor further includes a sensing material that is disposed on at least a portion of the transducer. The sensing material is configured to simultaneously exhibit a capacitance response and a resistance response in the presence of a gaseous agent. The sensor may be reversible, battery free, and may require no electrical contact with a sensor reader.

36 Claims, 8 Drawing Sheets

(56) References Cited

U.S. PATENT DOCUMENTS

| | | | | |
|---|---|---|---|---|
| 2007/0209937 | A1* | 9/2007 | Hoagland | G01N 27/122 |
| | | | | 204/424 |
| 2009/0020422 | A1* | 1/2009 | A. | G01N 33/0037 |
| | | | | 204/406 |
| 2010/0170325 | A1* | 7/2010 | Ren | G01N 27/127 |
| | | | | 73/31.05 |
| 2011/0101996 | A1 | 5/2011 | Potyrailo | |
| 2012/0161787 | A1* | 6/2012 | Potyrailo | G01N 27/02 |
| | | | | 324/652 |
| 2012/0166095 | A1 | 6/2012 | Potyrailo et al. | |
| 2012/0235690 | A1 | 9/2012 | Potyrailo et al. | |
| 2013/0052084 | A1* | 2/2013 | Potyrailo | G06K 19/0717 |
| | | | | 422/82.01 |
| 2013/0271159 | A1* | 10/2013 | Santos | G01R 27/2605 |
| | | | | 324/661 |
| 2014/0011286 | A1 | 1/2014 | Potyrailo et al. | |

OTHER PUBLICATIONS

Ishihara et al., "Sensitive detection of nitrogen oxides based upon capacitance changes in binary oxide mixture", Sensors and Actuators B: Chemical, vol. 30, Issue 1, pp. 43-45, Jan. 1, 1996.

Lampe et al., "New Materials for Metal Oxide Sensors", In Sensors Update, vol. 2, Issue 1, pp. 1 - 36, 1996.

Philipose et al., "Battery-Free Wireless Identification and Sensing", IEEE Pervasive Computing, vol. 4, Issue 1, pp. 37-45, Jan.-Mar. 2005.

Birdsell et al., "Wireless chemical sensors for high temperature environments", Solid-State Sensors, Actuators, and Microsystems Workshop, pp. 212-215, Jun. 4-8, 2006, Location: Hilton Head Island, South Carolina.

Luftman et al., "Chlorine Dioxide Gas Decontamination of Large Animal Hospital Intensive and Neonatal Care Units", Applied Biosafety, vol. 11, Issue 3, pp. 144-154, 2006.

Korotcenkov, "Metal oxides for solid-state gas sensors: What determines our choice?", Materials Science and Engineering: B, vol. 139, Issue 1, pp. 1-23, Apr. 25, 2007.

Fergus, "Perovskite oxides for semiconductor-based gas sensors", Sensors and Actuators B: Chemical, vol. 123, Issue 2, pp. 1169-1179, May 21, 2007.

Herran et al., "Solid state gas sensor for fast carbon dioxide detection", Sens. Actuators B, vol. 129, pp. 705-709, 2008.

Sayhan et al., "Discontinuously Operated Metal Oxide Gas Sensors for Flexible Tag Microlab Applications", IEEE Sensors Journal, vol. 8, pp. 176-181, 2008.

Steinberg et al., "Radio-Frequency Tag with Optoelectronic Interface for Distributed Wireless Chemical and Biological Sensor Applications", Sensors and Actuators B: Chemical, vol. 138, pp. 120-125, 2009.

Tricoli et al., "Minimal Cross-Sensitivity to Humidity During Ethanol Detection by SnO 2-TiO2 Solid Solutions", Nanotechnology, vol. 20, art. No. 315502, 2009.

Lee, "Gas Sensors Using Hierarchical and Hollow Oxide Nanostructures: Overview", Sens. Actuators B, vol. 140, pp. 319-336, 2009.

Courbat et al., "Ultra-low Power Metal-Oxide Gas Sensor on Plastic Foil", Transducers, pp. 584-587, 2009.

Yang et al., "Battery-Free RFID-Enabled Wireless Sensors", IEEE MTT-S International Microwave Symposium Digest (MTT), pp. 1528-1531, May 23-28, 2010.

Courbat, "Gas Sensors on Plastic Foil with Reduced Power Consumption for Wireless Applications", Thesis (Ph. D).-. Federal Polytechnic School of Lausanne, Jun. 10, 2010.

Carpenter, "Investigation of RFID Based Sensors for Sustainable Transportation Applications", University Transportation Research Center, Jan. 21, 2011.

Occhiuzzi et al., "RFID Passive Gas Sensor Integrating Carbon Nanotubes", IEEE Transactions on Microwave Theoryand Techniques, vol. 59, Issue 10, pp. 2674-2684, Oct. 2011.

Potyrailo et al., "Materials and Transducers Toward Selective Wireless Gas Sensing", Chemical Reviews, vol. 111, Issue 11, pp. 7315-7354, 2011.

Boura et al., "Communication and Powering Scheme for Wireless and Battery-Less Measurement", Radioengineering, vol. 21, Issue 1, Apr. 2012.

Carter et al., "Printed Low Power Amperometric Gas Sensors Employing RF Energy Harvesting", The Electrochemical Society, Abstract, 2012.

Liao et al., "Study on CuO-BaTiO3 Semiconductor Co2 Sensor", Sensors and Actuators B 80, Dec. 1, 2001, vol. 80, Issue 3, pp. 208-214.

Ishihara et al., "A New Type of CO2 Gas Sensor Based on Capacitance Changes", Sensors and Actuators B: Chemical, vol. No. 5, Issue No. 1-4, pp. 97-102, Aug. 1991.

European Search Report and Opinion issued in connection with corresponding EP Application No. 15199890.3 on Apr. 5, 2016.

* cited by examiner

MATERIALS AND SENSORS FOR DETECTING GASEOUS AGENTS

BACKGROUND

Embodiments of the invention relate to sensors and methods for the detection of gaseous agents, and more particularly to materials and sensors for the detection of chlorine dioxide, hydrogen peroxide, formaldehyde, peracetic acid, methyl bromide, ethylene oxide, ozone, and other gaseous agents that can be used as sterilization, fumigation, or decontamination agents.

Decontamination, fumigation, and sterilization of different environments is critical for a diverse range of applications including healthcare, food safety, and animal safety, for example. A number of gases can be used for the purposes of sterilization, fumigation, and decontamination including, but not limited to, chlorine dioxide, formaldehyde, hydrogen peroxide vapor, peracetic acid, methyl bromide, ozone, and ethylene oxide. These gases, as well as others, are known to be effective against both spore and non-spore forming bacteria.

Detection of gaseous agents that are utilized for decontamination, fumigation, and sterilization is critical for overall safety. It is beneficial to determine the presence of sterilizing agents to ensure that a given agent is performing adequately and that the surface or material being sterilized is free of harmful contaminants. For instance, measuring the presence of vapors by discerning a change in certain environmental variables within or surrounding a sensor may be particularly useful in monitoring changes in biopharmaceutical products, food, or beverages; monitoring industrial areas for chemical or physical hazards; security applications, such as residential home monitoring or home land security in airports; different environmental and clinical settings; and other public venues wherein detection of certain harmful and/or toxic vapors may be particularly useful. While current sensors offer a wide variety of both battery free and wireless sensors, there exists a commercial need for a reversible, battery-free sensor that requires no electrical contact with a sensor reader. Moreover, it is desired to have a sensor able to exhibit multiple responses to a change in an environmental parameter to eliminate sensor arrays.

The resistance change provided by semiconducting metal oxides when exposed to a vapor, for example, is either an up or down change. Traditionally, sensor arrays that include multiple sensors for functional and accurate monitoring are utilized. Many sensor arrays include a number of identical transducers coated with different sensing materials. However, while using identical transducers simplifies fabrication of the sensor array, such an array may have limited capabilities for sensing only a single response (e.g. resistance, current, capacitance, work function, mass, optical thickness, light intensity, etc). In certain applications, multiple responses or changes in multiple properties may occur. In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, however, fabricating a sensor array having individual sensors uniquely fabricated to sense a particular response complicates fabrication of the array and is uneconomical. Therefore, a single sensor that comprises a sensing material that can simultaneously exhibit more than one response when in the presence of an analyte is desired.

Various embodiments disclosed herein may address one or more of the challenges set forth above.

BRIEF DESCRIPTION

In one embodiment, a sensor is configured to detect a gaseous agent, and the sensor has a transducer, which includes an electrical resonant circuit that forms an antenna. The sensor also has a sensing material disposed at least on a portion of the transducer, and the sensing material is configured to simultaneously exhibit a capacitance response and a resistance response when exposed to a gaseous agent.

In another embodiment, a sensor is configured to detect a gaseous agent and the sensor has a transducer, which includes an antenna. The sensor also has a sensing material disposed on the transducer, and the sensing material includes a semiconducting metal oxide. Also, a noble metal catalyst is deposited on the semiconducting metal oxide. The antenna is configured to emit an electric field to probe a response of the sensing material when exposed to a gaseous agent.

In another embodiment, a method for manufacturing a sensor configured to detect a gaseous agent is described. First, a transducer is formed by disposing an antenna on a substrate. Second, a noble metal catalyst is doped to a semiconducting metal oxide to form a metal oxide powder. Third, the metal oxide powder is mixed with an aqueous solution of a polymer matrix to form a stable metal oxide suspension. Fourth, the metal oxide suspension is deposited on the transducer and dried to form a final sensing material.

In another embodiment, a method for detecting a gaseous agent is recited. In one step, a sensing material is exposed to a gaseous agent, wherein the sensing material comprises a first component and a second component. The first component and the second component are deposited on a surface of a sensing coil. The first component and/or the second component are oxidized or reduced, and a capacitance response and a resistance response of the sensing coil are measured over a frequency range. Finally, an analysis is performed using the capacitance response and the resistance response to detect a concentration of the gaseous agent.

DRAWINGS

These and other features, aspects, and advantages of the present disclosure will become better understood when the following detailed description is read with reference to the accompanying drawings in which like characters represent like parts throughout the drawings, wherein.

Figure 9A:
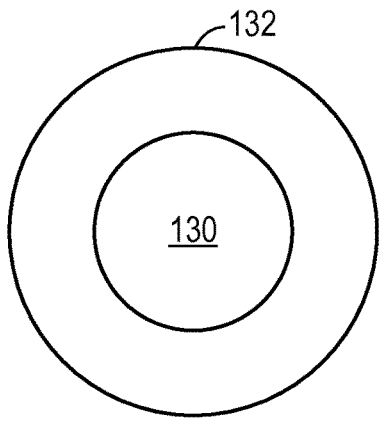
Figure 9B:
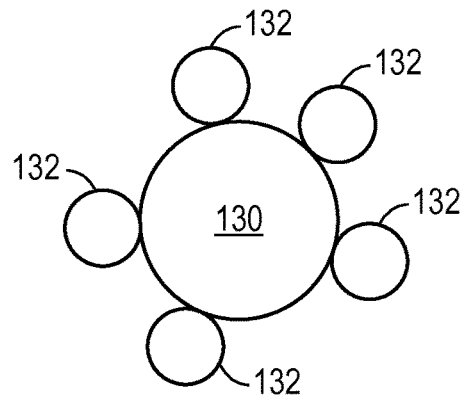
Figure 9C:
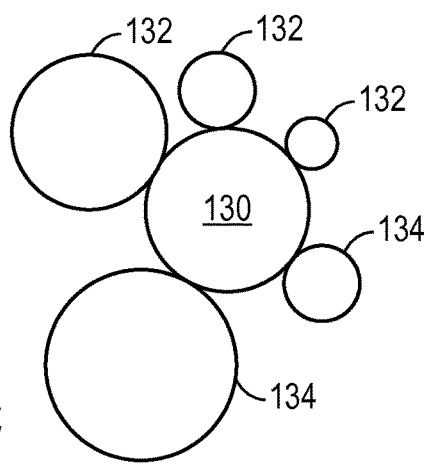
Figure 10:
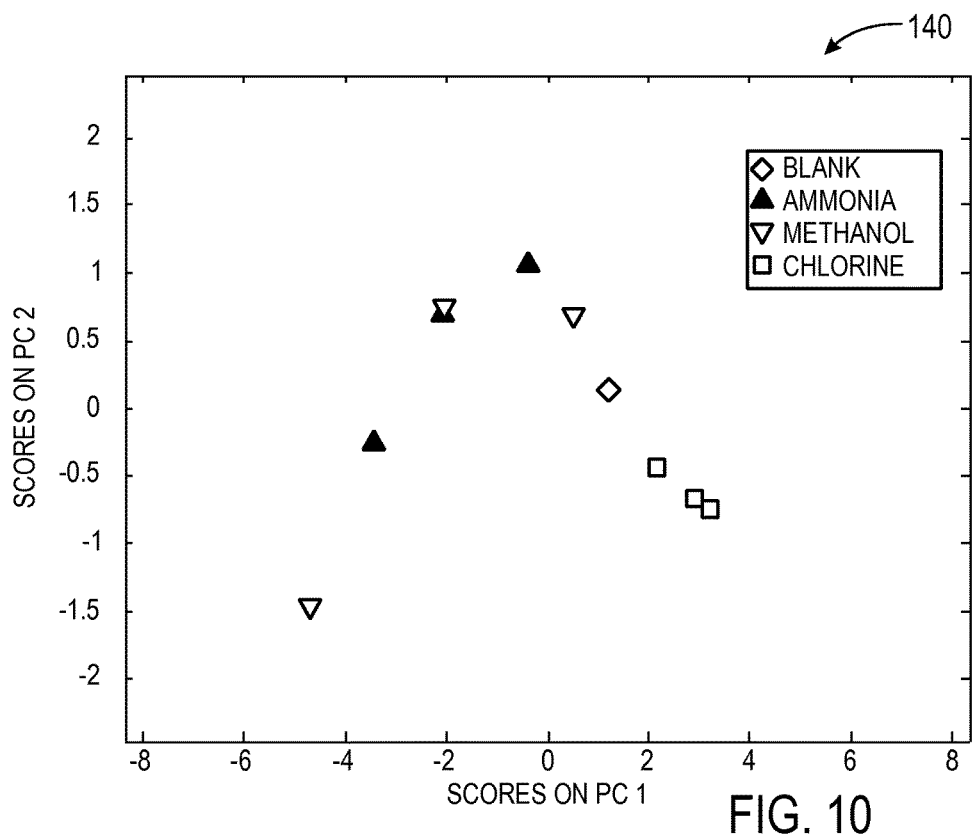
Figure 11:
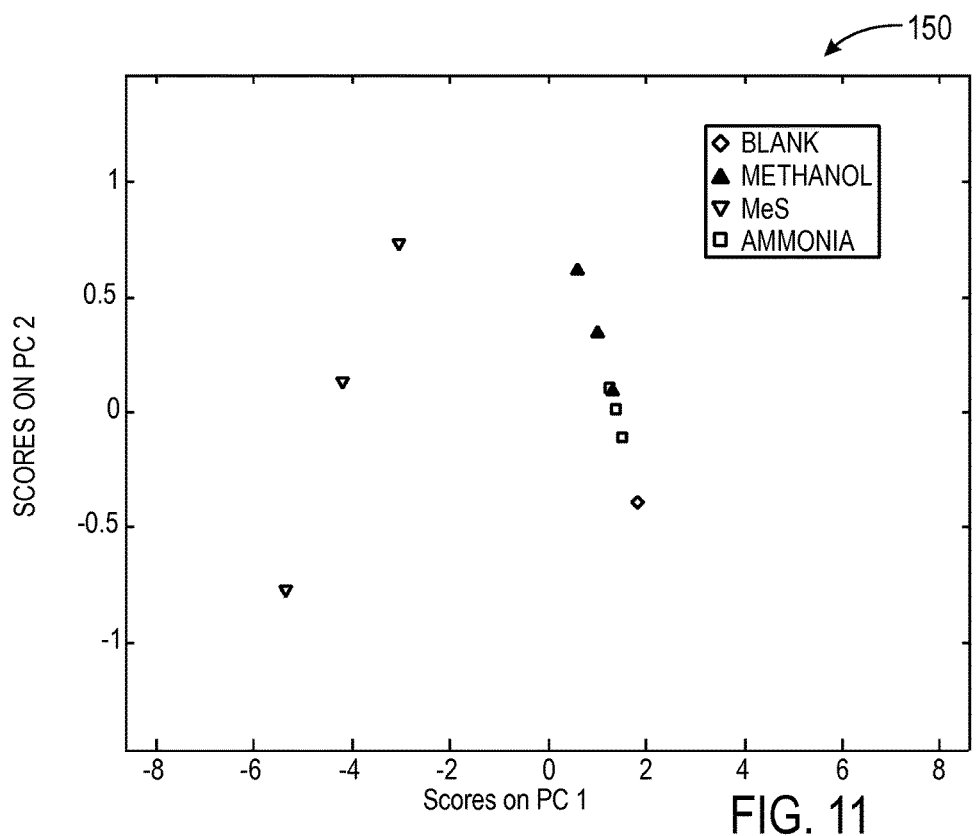
Figure 12:
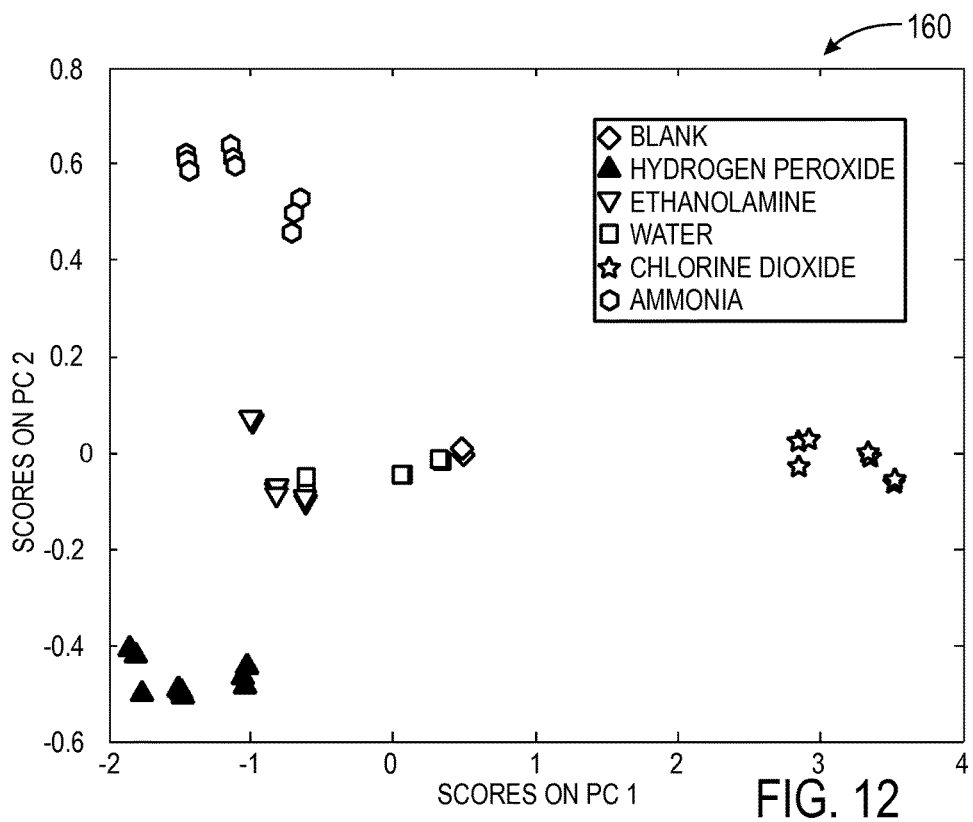
Figure 13:
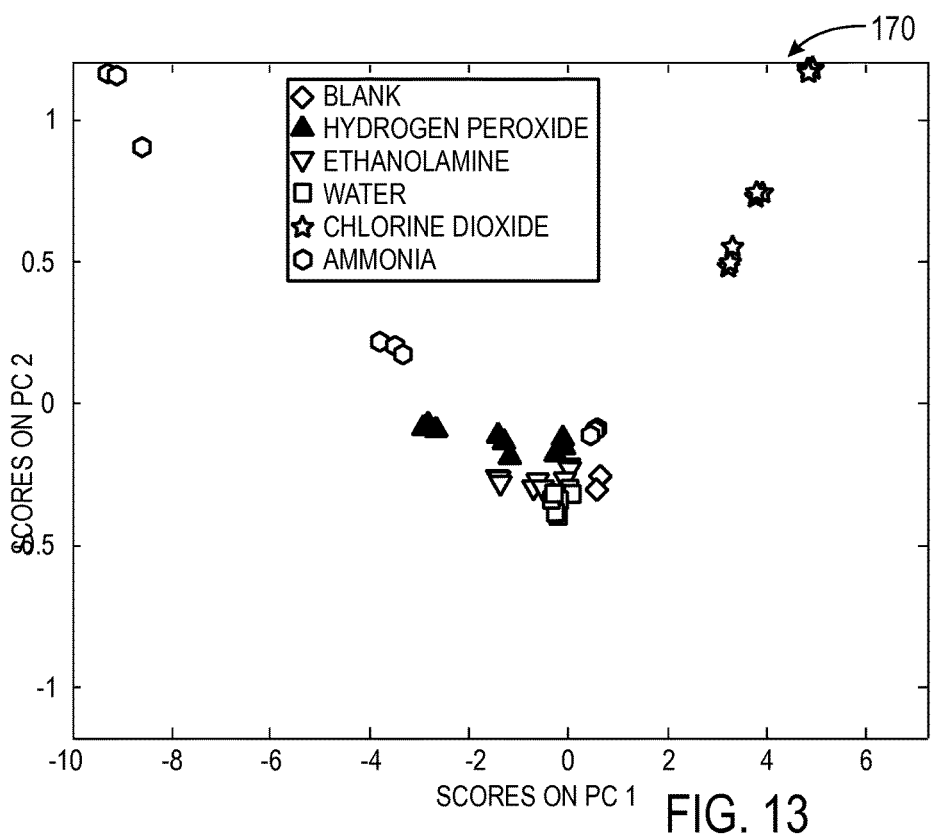
Figure 14:
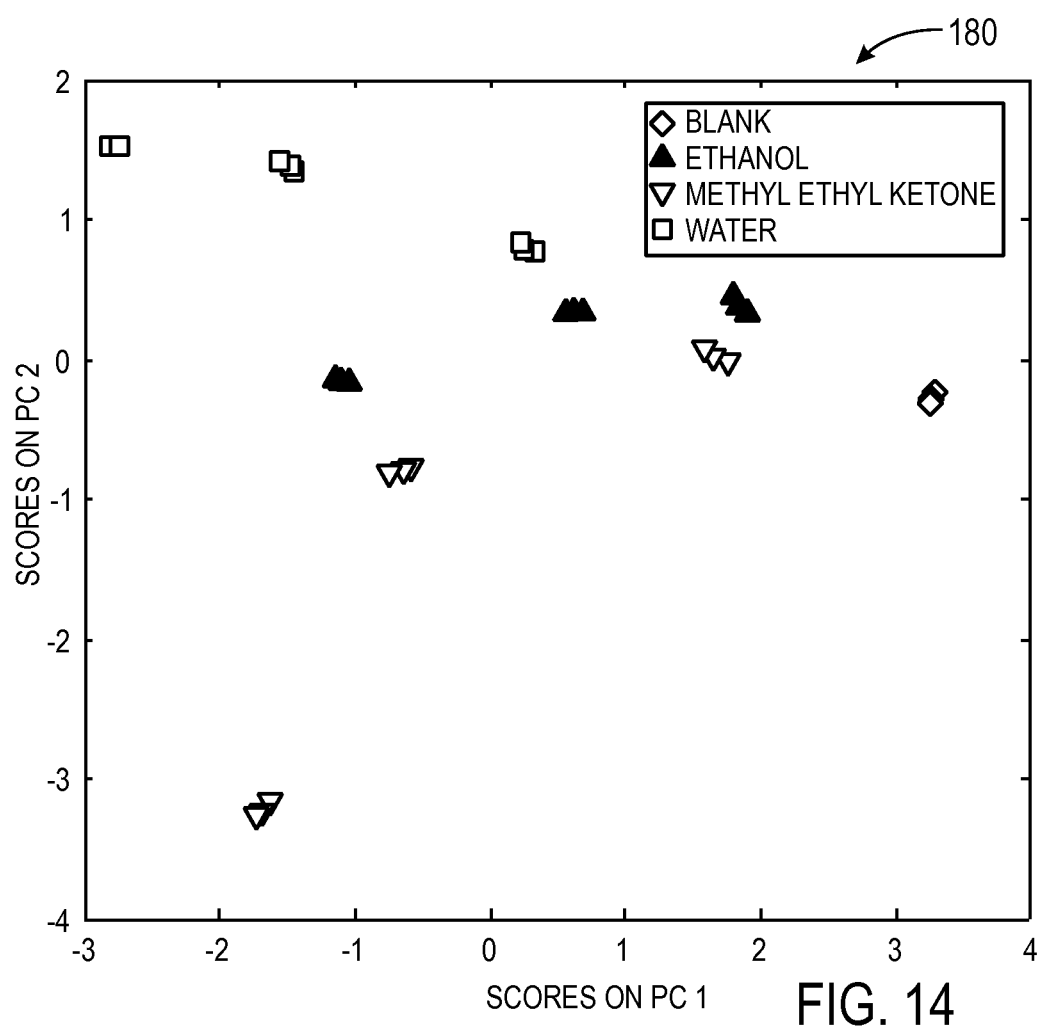

FIG. 9A illustrates an embodiment of a design of a sensing material that may be used with a multivariable sensor, FIG. 9B illustrates another embodiment of a design of a sensing material that may be used with a multivariable sensor, and FIG. 9C illustrates yet another embodiment of a design of a sensing material that may be used with a multivariable sensor, in accordance with embodiments of the present disclosure;

FIG. 10 is a graphical representation of experimental results obtained with one resonant sensor upon exposure of the sensor to three different vapors, in accordance with embodiments of the present disclosure;

FIG. 11 is a graphical representation of experimental results obtained with another resonant sensor upon exposure of the sensor to three different vapors, in accordance with embodiments of the present disclosure;

FIG. 12 is a graphical representation of experimental results obtained with one resonant sensor upon exposure of the sensor to five different vapors, in accordance with embodiments of the present disclosure;

FIG. 13 is a graphical representation of experimental results obtained with another resonant sensor upon exposure of the sensor to five different vapors, in accordance with embodiments of the present disclosure;

FIG. 14 is a graphical representation of experimental results obtained with one resonant sensor upon exposure of the sensor to three different vapors, in accordance with embodiments of the present disclosure.

DETAILED DESCRIPTION

In various embodiments, a sensing material may be disposed on a surface of a device configured as a resonant circuit, such as an inductor-capacitor-resistor ("LCR") sensor. Non-limiting examples of LCR sensors include RFID sensors with an integrated circuit ("IC") memory chip and RFID sensors without an IC memory chip (e.g., chipless RFID sensors or chipless LCR sensors). LCR sensors can be wireless or wired. In order to collect data, an impedance spectrum of a resonant circuit is acquired over a frequency range, such as the resonant frequency range of the LCR circuit. In certain embodiments, an impedance response of the resonant circuit is acquired at a single frequency within the resonant frequency range of the LCR circuit. The technique further includes calculating the multivariate signature from the acquired spectrum and manipulating the data to discern the presence of certain vapors. The presence of vapors is detected by measuring the changes in dielectric, dimensional, charge transfer, and other changes in the properties of the materials employed by observing the changes in the resonant electronic properties of the circuit. By using multivariate analysis, a sensing material's response to the presence of a gaseous sterilization agent can be simplified to a single data point allowing for recognition or detection of a gaseous agent. In certain embodiments, calibration models based on univariate analyses are also used for recognition of a specific gas presence and its concentration.

To more clearly and concisely describe the subject matter of the claimed invention, the following definitions are provided for specific terms, which are used in the following description and the appended claims.

The term "fluids" includes gases, vapors, liquids, and solids.

The term "analyte" includes any substance or chemical constituent that is the subject of a chemical analysis. Examples of analytes include, but are not limited to, chlorine dioxide, formaldehyde, hydrogen peroxide, peracetic acid, methyl bromide, ozone, ethylene oxide, or any combination thereof. In certain embodiments, the sensing materials of the present disclosure may be configured to detect analytes related to "decontamination," "sterilization," and/or "fumigation." The terms "decontamination," "sterilization," and "fumigation" are interrelated and may all refer to a process, method, procedure, or course of action related to removing a contaminant, undesired substance, or other fluid from an environment. For example, a decontamination, sterilization, and/or fumigation procedure may involve using a substance (e.g., chlorine dioxide) to eliminate a contaminant (e.g., bacteria) via a chemical reaction, response, or process.

The term "monitoring process" includes, but is not limited to, measuring physical changes that occur around the sensor. For example, monitoring processes including monitoring changes in a biopharmaceutical, food, or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response.

The term "multivariable sensor" is referred to herein as a single sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. In certain embodiments, the multiple response signals comprise a change in a capacitance and a change in a resistance of a sensing material disposed on a multivariable sensor when exposed to an analyte. In other embodiments, the multiple response signals comprise a change in a capacitance, a change in a resistance, a change in an inductance, or any combination thereof.

The term "multivariate analysis" refers to a mathematical procedure that is used to analyze more than one variable from the sensor response and to provide the information about the type of at least one environmental parameter from the measured sensor parameters and/or to quantitative information about the level of at least one environmental parameter from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "environmental parameters" is used to refer to measurable environmental variables within or surrounding a manufacturing or monitoring system. The measurable environmental variables comprise at least one of physical, chemical, and biological properties and include, but are not limited to, measurement of temperature; pressure; material concentration; conductivity; dielectric property; number of dielectric, metallic, chemical, or biological particles in the proximity or in contact with the sensor; dose of ionizing radiation; and light intensity.

The term "spectral parameters" is used to refer to measurable variables of the sensor response. The sensor response is the impedance spectrum of the LCR or RFID sensor. In addition to measuring the impedance spectrum in the form of Z-parameters, S-parameters, and other parameters, the impedance spectrum (its both real and imaginary parts) may be analyzed simultaneously using various parameters for analysis, such as, the frequency of the maximum of the real part of the impedance ($F_p$), the magnitude of the real part of the impedance ($Z_p$), the resonant frequency of the imaginary part of the impedance ($F_1$), the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra may also be called "features" or "descriptors." The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

The term "resonance impedance" or "impedance" refers to measured sensor frequency response as real and imaginary parts of impedance around the resonance of the sensor from which the sensor "spectral parameters" are extracted.

As used herein the term "sensing materials and sensing films" includes, but is not limited to, materials deposited onto a transducer's electronics module, such as LCR circuit components or an RFID tag, to perform the function of predictably and reproducibly affecting the impedance sensor response upon interaction with the environment. In order to prevent the material in the sensor film from leaching into the liquid environment, the sensing materials are attached to the sensor surface using standard techniques, such as covalent bonding, electrostatic bonding, and other standard techniques known to those of ordinary skill in the art.

The terms "transducer and sensor" are used to refer to electronic devices such as RFID and LCR devices intended for sensing. "Transducer" is a device before it is coated with a sensing film or before it is calibrated for a sensing application. "Sensor" is a device typically after it is coated with a sensing film and after being calibrated for the sensing application.

As used herein the term "RFID tag" refers to an identification and reporting technology that uses electronic tags for identifying and/or tracking articles to which the RFID tag may be attached. An RFID tag typically includes at least two components where the first component is an integrated circuit (IC) memory chip for storing and processing information and modulating and demodulating a radio frequency signal. This memory chip can also be used for other specialized functions, for example, it can contain a capacitor. It can also contain at least one input for an analog signal such as resistance input, capacitance input, or inductance input. In the case of a chipless RFID tag, the RFID tag may not include an IC memory chip. This type of RFID tag may be useful in applications where an RFID tag does not need to be identified, but rather a signal merely indicating the presence of the tag provides useful information (e.g., product security applications). The second component of the RFID tag is an antenna for receiving and transmitting the radio frequency signal.

The term "RFID sensor" is an RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID tag with a sensing film, the electrical response of the film is translated into simultaneous changes to the impedance response, resonance peak position, peak width, peak height, and peak symmetry of the impedance response of the sensor antenna; magnitude of the real part of the impedance; resonant frequency of the imaginary part of the impedance; anti-resonant frequency of the imaginary part of the impedance; zero-reactance frequency; phase angle; and magnitude of impedance. The "RFID sensor" can have an integrated circuit (IC) memory chip attached to the antenna or can have no IC memory chip. An RFID sensor without an IC memory chip is an LCR sensor. An LCR sensor is comprised of known components, such as at least one inductor (L), at least one capacitor (C), and at least one resistor (R) to form an LCR circuit.

The term "reversibility" with respect to sensor operation as referred to herein, is when the sensor returns back to its natural, or pre-exposure, value as a result of the metal oxide composition or any other sensing material composition preventing permanent changes to the sensor. Thus, in the presence of a vapor, the sensor will respond accordingly; however, as the vapor concentration dissipates the sensor response will return to the original value. Thus, the sensing material is said to be reversible when the material exhibits a signal change upon contact with a desired gas and returns back to its original, pre-exposure, value upon removal of the gas. Conversely, the sensing material is said to be non-reversible when the material exhibits a signal change upon contact with a desired gas and does not return to its original value upon removal of the gas concentration.

The term "dosimeter" with respect to sensor operation refers to a sensor that exhibits a cumulative signal change when exposed to increasing concentrations of the vapor. The sensor signal increases as the vapor concentration increases, but the signal does not return to its original value upon the removal of vapor. In one embodiment, a dosimeter sensor may be configured as a one-time use sensor.

The term "writer/reader" includes, but is not limited to, a combination of devices to write and read data into the memory of a memory chip and to read impedance of the antenna. Another term for "writer/reader" is "interrogator."

The term "preparing" with respect to a method for constructing a sensor or sensing device refers to assembling, building, creating, gathering the components for, partially constructing, and/or completing a partial construction of a sensor or sensing device as recited in the present disclosure.

In accordance with embodiments disclosed herein, an LCR sensor or an RFID sensor for sensing gaseous agents is described. As previously discussed, semiconducting metal oxide sensing materials can be disposed on a transducer and used to detect the presence of particular vapors. When an analyte comes into the presence of the semiconducting metal oxide, the gaseous analyte may undergo oxidation, reduction, adsorption, desorption, or bulk effects, which thereby cause a change in resistance, a change in capacitance, and/or a change in inductance of the semiconducting metal oxide. In accordance with embodiments disclosed herein, changes in at least two of the semiconducting metal oxide's dielectric properties can be simultaneously measured through inductive coupling of a sensor reader to a sensing coil with a deposited sensing material, which can detect the presence of chlorine dioxide or other gaseous agents. In certain embodiments, the sensing coil can serve as a sensing antenna.

Figure 1A:
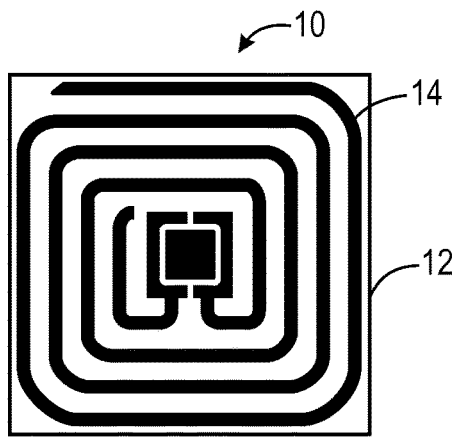
FIG. 1A shows an RFID tag to be used for vapor sensing.

Referring now to the figures, FIG. 1 shows two embodiments wherein a sensor is specifically adapted to detect gaseous agents. FIG. 1A illustrates one embodiment, wherein the sensor 10 comprises a radio frequency identification (RFID) platform as a transducer. Additionally, the sensor 10 comprises a sensing material 12 disposed upon an antenna 14, thereby altering the impedance response of the sensor 10 when in the presence of a vapor. In another embodiment, the transducer may be an inductor-capacitor-resistor (LCR) resonator, a thickness shear mode resonator, an interdigital electrode structure, or a general electrode structure. In one embodiment, the transducer may function over a frequency range from several kilohertz (kHz) to several petahertz (PHz).

Figure 1B:
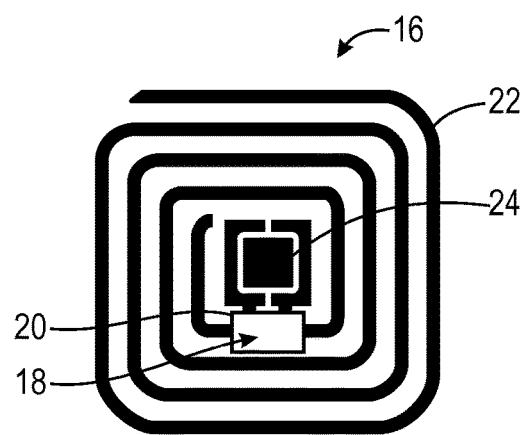
FIG. 1B shows another embodiment of an RFID tag with a complementary sensing region, in accordance with embodiments of the present disclosure.

FIG. 1B illustrates another embodiment comprising a sensor 16 with an RFID platform as a transducer. In contrast to FIG. 1A, a sensing material 18 is disposed only upon a complementary sensing region 20 of the sensor 16, rather than disposed on the entire antenna 22. The complementary sensing region 20 is the region of the sensor 16 where the antenna 22 and an integrated circuit ("IC") memory chip 24 come in contact, or overlap. The sensing material 18 disposed on the complementary sensing region 20 alters the impedance response of the sensor 16 when in the presence of a vapor. In another embodiment, the transducer used may be an inductor-capacitor-resistor (LCR) resonator, a thickness shear mode resonator, an interdigital electrode structure, or a general electrode structure.

The complementary sensing region 20 provides an advantage over the configuration shown in FIG. 1A, wherein the entire antenna 14 serves as an electrode structure. The relatively small size of the complementary sensing region 20 when compared to the whole antenna 22 leads to reduced costs of the applied sensing material. Also, it is relatively simple to fabricate a nanoscale size gap between electrodes in the complementary sensing region 20 as compared to the gap between electrode regions on the antenna 14 as shown in FIG. 1A. Non-limiting examples of complementary sensors are interdigitated sensors, resistive sensors, and capacitive sensors. Complementary sensors are described in U.S. Pat. No. 7,911,345 entitled "Methods and Systems for Calibration of RFID Sensors," which is incorporated herein by reference.

For the detection of chlorine dioxide and other such oxidizers, both the sensing systems shown in FIGS. 1A and 1B can be utilized, with selection being dependent on the needed sensitivity, response time, sensor cost, and other performance and/or manufacturing parameters.

In one embodiment, the sensing material 12 utilized is a semiconducting metal oxide formulation that is tailored to specifically detect a desired analyte. As a non-limiting example, the sensing material 12 used for chlorine dioxide includes a noble metal catalyst disposed on the semiconducting metal oxide. The semiconducting metal oxide may include Indium oxide ($In_2O_3$), Zinc oxide (ZnO), Tungsten oxide ($WO_3$), Tin oxide ($SnO_2$), Titanium oxide ($TiO_2$), and Indium Tin oxide (ITO). The noble metal catalyst can be any of the following: Platinum (Pt), Palladium (Pd), Gold (Au), and Silver (Ag). In certain embodiments, the sensing material 12 may consist of a core component and a layer, shell, or matrix component(s) as described in detail with respect to FIG. 9.

In certain embodiment, a method of preparation of the sensing material includes first doping the noble metal catalyst to the surface of the semiconducting metal oxide by wetness impregnation to form a metal oxide powder. In other embodiments, the noble metal catalyst may be doped to the semiconducting metal oxide using in-situ synthesis. Doping in general refers to introducing controlled amounts of impurities to a base composition to alter its electrical properties to achieve a desired material performance. Hence, the noble metal catalyst is disposed on the semiconducting metal oxide to change the electrical properties of the basic semiconducting metal oxide. In one embodiment, adding the noble metal catalyst to the semiconducting metal oxide causes the semiconducting metal oxide to simultaneously exhibit multiple responses when in the presence of a vapor. After the noble metal catalyst is doped to the semiconducting metal oxide, the resulting metal oxide powder is mixed with an aqueous solution of metal salts. Non-limiting examples of such metal salts are gold chloride, hydrogen hexachloroplatinate, silver nitrate, and palladium chloride. Finally, the final material powders are dried at a controlled temperature between 450-600° C. to promote decomposition of the metal precursor into the metallic form. In one embodiment, the weight percentage of the additive to the base metal oxide within the sensing material is in the range of 0.01% to 1%.

Semiconducting metal oxides can be synthesized through different approaches such as sol-gel, hydrothermal reaction, and any others known in the art. In certain embodiments, $SnCl_4$ can be used as the source of Tin to create Tin oxide ($SnO_2$). $SnCl_4$ may be dissolved in a water:ethanol (1:1 wt/wt) solvent, wherein a few drops of hydrogen chloride solution are added until the pH is approximately 0.4. The pH of the resulting solution can be adjusted to 4.0 by adding 30% $NH_4OH$ while constantly stirring the mixture. The resulting precipitate is then filtered and washed with water until free of any $Cl^-$, and then initially dried at 100° C. for 2 hours followed by calcination at 600° C. for 4 hours.

In other embodiments, a mixture of Zinc oxide and Tungsten oxide can be fabricated by dissolving 3.00 g sodium tungstate ($Na_2WO_4.2H_2O$) and 0.05 g hexadecyl trimethyl ammonium bromide ("CTAB") in 10 mL of deionized ("DI") water. Next, 10 mL of nitric acid (1.5 mol/L) solution may slowly be added into this solution, and the resulting solution may be stirred for 2 hours. The precipitate produced can be collected by centrifugation. The precipitate is then washed twice with DI water, washed three times with ethanol, and dried in an oven at 80° C. to produce tungstenic acid. Next, 3.67 g $Zn(NO_3)_2$ and 0.10 g CTAB are dissolved in 50 mL of DI water to obtain solution "A." Additionally, Na$_2$CO$_3$ (1.31 g) can also be dissolved in 50 mL of DI water to obtain solution "B." Solution B can then be added, drop wise, to solution A with vigorous stirring. After stirring for 1 hour, the precipitate is collected by centrifugation. Then, an appropriate amount of the formed tungstenic acid can be mixed with zinc hydroxyl carbonate, and the mixture may be ground for 0.5 hours. The mixture should finally be calcined at 600° C. for 2 hours in air.

In certain embodiments, the semiconducting metal oxide doped with the noble metal catalyst can be dispersed directly in a solvent (e.g., water, ethanol, isopropyl alcohol, acetone, toluene, hexane and 1-Methyl-2-Pyrrolidinone (NMP), or a combination thereof). The solvent includes a polymer matrix such as polyvinylidene fluoride (PVDF), polyvinyl alcohol (PVA), and acrylic based polymers using a deposition method. Some deposition methods include, but are not limited to, drop casting, spray coating, spin coating, flood coating, inkjet printing, direct writing, ink deposition, and screen printing. The weight percentage of the polymer matrix to the semiconducting metal oxide within the sensing material is in the range from 0.1% to 99.9%, more preferably from 1% to 99%, and more preferably from 10% to 80%. The matrix can be a polymer matrix, an inorganic matrix, or a composite matrix.

The combination and the ratio of the polymer matrix to the semiconducting metal oxide in the composition may determine sensing performance. In one embodiment, a desired sensing performance may be to achieve a sensor response when the sensor is exposed to an analyte concentration of about 30 ppm to about 300 ppm without exhibiting a response saturation at about 300 ppm. To develop a sensor that may achieve the desired sensing performance, a polymer matrix may be mixed with an active sensing material composed of Indium Tin oxide to form a stable dispersion in solvent. The polymer matrix-semiconducting metal oxide dispersion can be deposited onto the RFID transducer surface and dried to form sensing films. Table 1 shows sensing performances of three different polymer matrix-semiconducting metal oxide formulations for ClO$_2$ sensing. Approximately 30 weight percent of the film was polymer. The $Z_p$ values of the sensors before sensor film deposition were 800 ohm. Among the three polymer matrices tested, PVDF demonstrated excellent compatibility with Indium Tin oxide and achieved the best ClO$_2$ detection sensitivity (dynamic resolution between 30-300 ppm).

TABLE 1

Sensing performance of three sensors with different polymer matrices and Indium Tin oxide for ClO$_2$ detection

| Sensor with polymer matrix | Sensor 1 with PVA | Sensor 2 with PVDF | Sensor 3 with UV Acrylate |
|---|---|---|---|
| Film quality | Fair | Good | Fair |
| Difference in Zp before and after sensor film deposition, Ohm | 800 − 800 = 0 | 800 − 350 = 450 | 800 − 650 = 150 |
| ClO$_2$ sensing performance at 300 ppm | No response | Strong response | Weak response |

Table 2 shows sensor performance when different percentages of PVDF are included in the sensing film. The 67% PVDF and 33% Indium Tin oxide combination achieved the most favorable ClO$_2$ response from 30 to 300 ppm of ClO$_2$ because it did not exhibit saturation at 300 ppm while other sensing films exhibited saturation at concentrations less than 300 ppm. Sensors with the formulation containing 67% of PVDF also demonstrated reproducible sensor responses to the concentrations tested.

TABLE 2

Sensing performance of sensors with different percentages of PVDF in the sensing film

| weight % of polymer in the film | ClO$_2$ sensor response |
|---|---|
| 19% | saturates above 110 ppm |
| 28% | saturates above 180 ppm |
| 38% | saturates above 200 ppm |
| 55% | saturates above 200 ppm |
| 67% | saturates above 300 ppm |
| 86.07% | Response is small because of poor sensing film quality |

Metal oxide sensors may contain a metal oxide, a catalyst, and a polymer, where the polymer serves as a binder. The polymer binder improves adhesion of the sensing material to the substrate. In certain embodiments, the sensing material may contain a metal oxide, a catalyst, and a polymer, where the polymer serves as a matrix to control sensor sensitivity.

Figure 2:
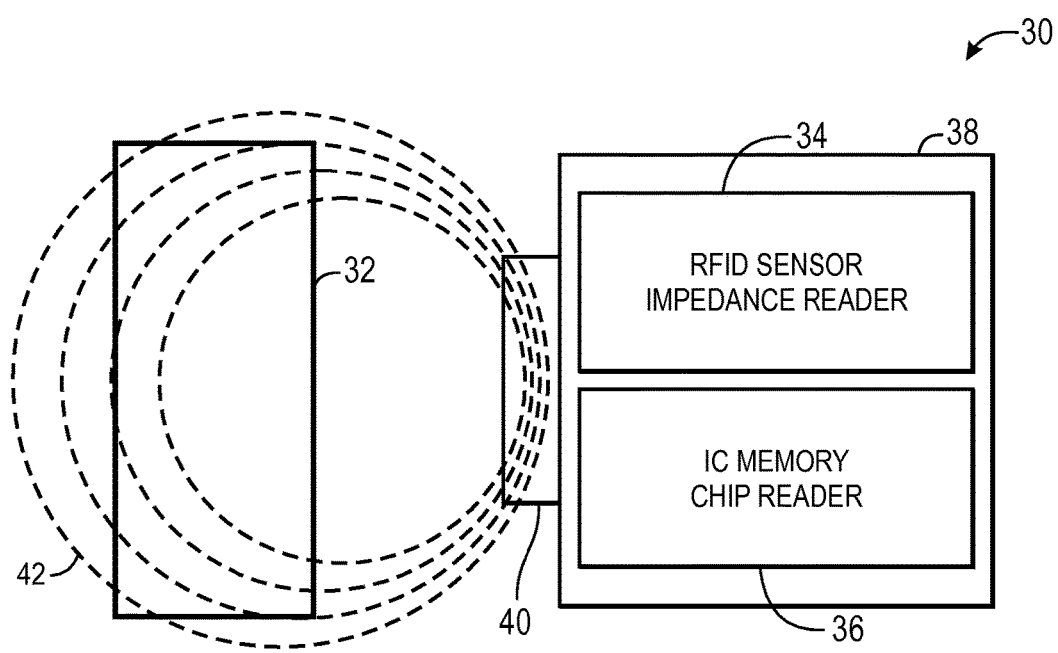
FIG. 2 is a schematic representation of a sensor, in accordance with embodiments of the present disclosure.

FIG. 2 shows one embodiment of a complete system 30 configured to detect the presence of certain gaseous analytes. In certain embodiments, a sensor 32 with a passive, or battery-free, RFID platform transducer is exposed to a gaseous analyte. An RFID sensor impedance reader 34 and an IC memory chip reader 36 are housed within an RFID reader 38. A sensing coil 40 emits a magnetic field 42 in order to read the sensor's response to the analyte. In the presence of the analyte, the sensing material disposed on the sensor 32 may incur a change in capacitance and a change in resistance, which the sensing coil's magnetic field 42 will detect. This process, in effect, writes and reads information onto the IC memory chip reader 34 while measuring the impedance Z(f) of the sensor 32 via inductive coupling between the sensing coil 40 and the sensor 32. In another embodiment the sensor transducer may be an inductor-capacitor-resistor (LCR) resonator, a thickness shear mode resonator, an interdigital electrode structure, or a general electrode structure.

Figure 3:
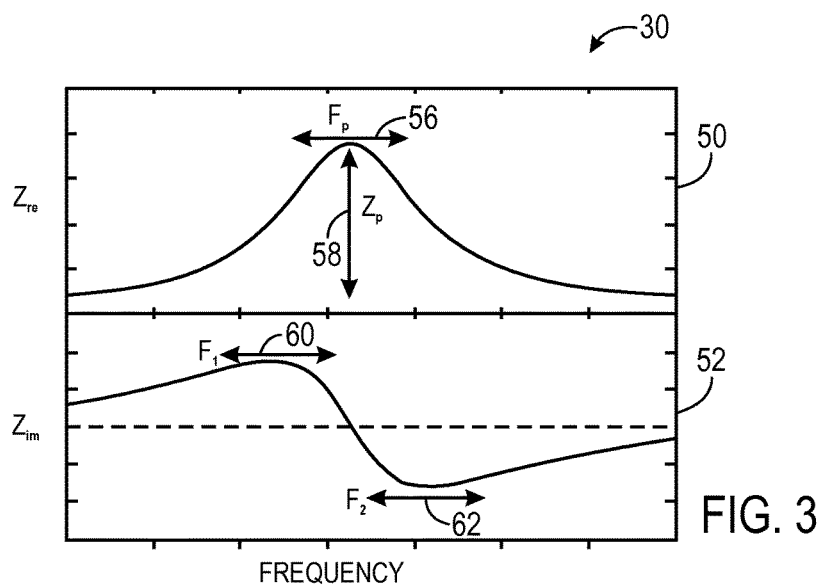
FIG. 3 is a graphical representation of a measured impedance spectrum, in accordance with embodiments of the present disclosure.

FIG. 3 shows an example of a measured impedance spectrum containing real parts $Z_{re}(f)$ 50 and imaginary parts $Z_{im}(f)$ 52 of the impedance spectrum 54. Furthermore, examples of the various spectral parameters utilized for multivariate analysis are shown—frequency position (F$_p$) 56; magnitude of $Z_{re}(f)$ (Z$_p$) 58; resonant frequency of $Z_{im}(f)$ (F$_1$) 60; and antiresonant frequency of $Z_{im}(f)$ (F$_2$) 62. To accurately measure gases in the presence of uncontrolled temperature fluctuations, the real $Z_{re}(f)$ 50 and imaginary $Z_{im}(f)$ 52 parts of the impedance spectra Ž(f) 54 are measured from the resonant sensor antenna coated with a sensing material and several spectral parameters are calculated from the measured $Z_{re}(f)$ 50 and $Z_{im}(f)$ 52 as shown in FIG. 3. Multivariate analysis reduces the dimensionality of the complex impedance response from measured real $Z_{re}(f)$ 50 and imaginary $Z_{im}(f)$ 52 parts of the complex impedance spectra 54, or calculated parameters F$_p$ 56, Z$_p$ 58, F$_1$ 60, F$_2$ 62, to a single data point in multidimensional space. The single data point can identify an analyte that was present, while taking into account any fluctuations in ambient temperature. Self-correction against fluctuations of ambient temperature with multivariable sensors is described in U.S.

Patent Application 2012/0161787 entitled Temperature-Independent Chemical and Biological Sensors, which is incorporated herein by reference.

In one embodiment, multivariate analysis is performed as principal components analysis ("PCA"). PCA is a mathematical procedure that is used to reduce multidimensional data sets to lower dimensions (e.g., a single variable) to simplify analysis. Principal component analysis is a part of eigenanalysis methods of statistical analysis of multivariate data and may be performed using a covariance matrix or correlation matrix. Upon applying PCA, a multivariate signature of the sensor response to different vapors is produced. Principal component analysis with respect to data received from a sensor is described in U.S. Pat. No. 8,364,419 entitled Sensor Systems and Methods for Selective Analyte Detection Using Resonance Sensor Circuit, which is incorporated herein by reference.

Figure 4:
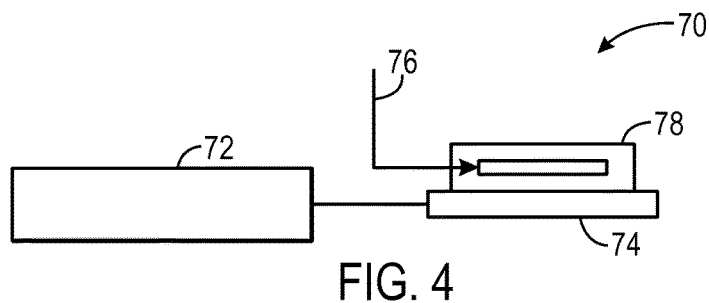
FIG. 4 is a block schematic of a sensor setup, in accordance with embodiments of the present disclosure.

FIG. 4 shows an embodiment of an experimental setup 70, wherein a sensor reader 72 is attached to a pick up coil 74, and a sensor 76 is housed within a gas flow cell 78 which is placed atop the pick up coil 74. The sensor 76 may be a sensing coil or an antenna with a deposited sensing film. The experimental setup 70 was used to obtain experimental data, as described further with reference to FIGS. 5, 6, and 10-14. In one embodiment, an analyte flow is controlled through the gas flow cell 78 to expose the sensor to a controlled concentration of analyte. The gas flow cell 78 may be an air-tight, plastic box with an inlet and outlet for the analyte flow. When the analyte enters the gas flow cell 78, the sensor 76 can detect the analyte, whereby the sensing material may exhibit a simultaneous response in an altered capacitance and resistance. The pick up coil 74 detects the change in capacitance and resistance of the sensing material deposited onto the sensing coil or antenna 76 via inductive coupling between the pick up coil 74 and the sensor 76. The sensor reader 72 then collects this data and performs multivariate or univariate analysis to alert the operator to the presence of the analyte.

FIG. 5 shows a graphical representation of the results from testing an embodiment of the invention, and specifically, FIG. 5 illustrates the reproducibility of a sensor response with regard to the above mentioned experimental setup 70. For purposes of the experiment, generation of different concentrations of chlorine dioxide gas were accomplished using a computer controlled vapor generation system. The $ClO_2$ was generated by a sodium chlorite-hydrochloric acid reaction, with the principle, working chemical reaction being:

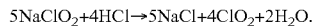

$$5NaClO_2 + 4HCl \rightarrow 5NaCl + 4ClO_2 + 2H_2O.$$

Figure 5A:
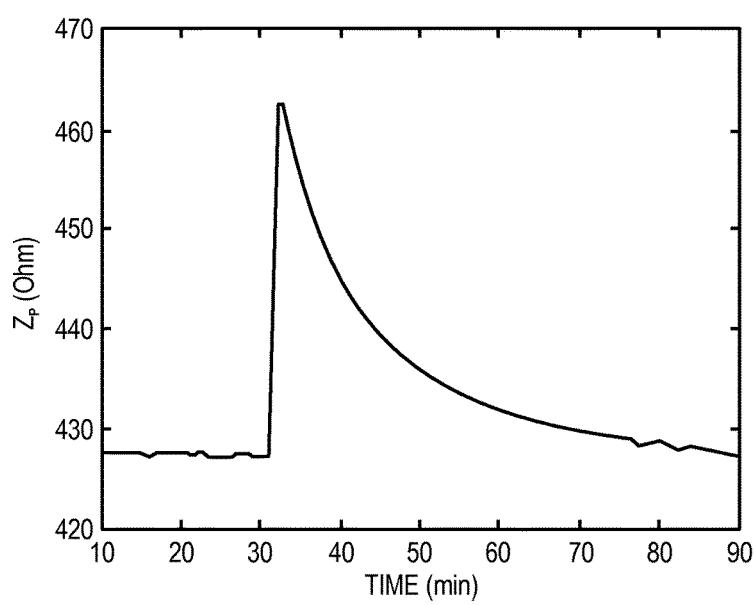
FIG. 5A is a graphical representation of an experimental result obtained with a first sensor.
Figure 5B:
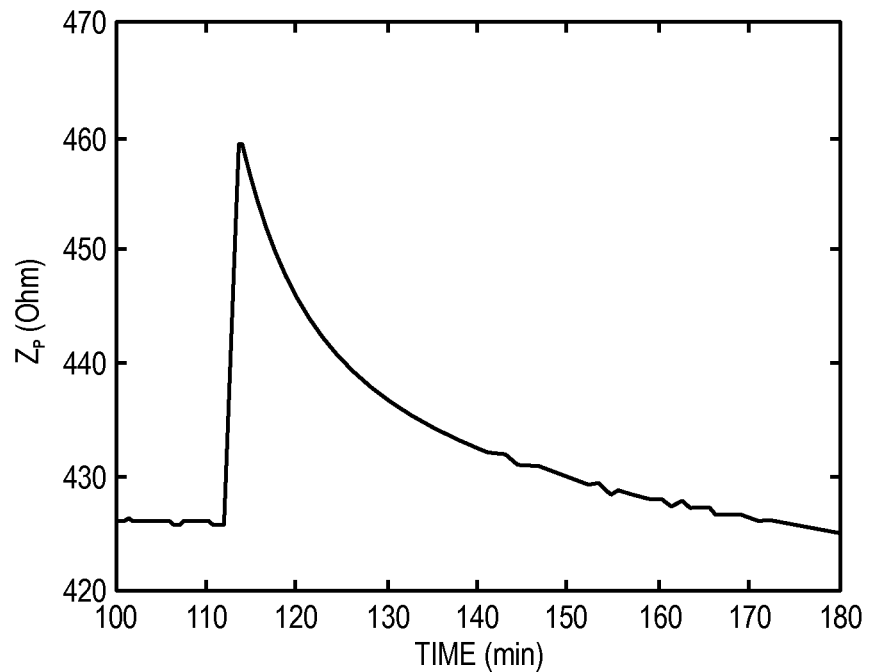
FIG. 5B is a graphical representation of an experimental result obtained with a second sensor.
Figure 5C:
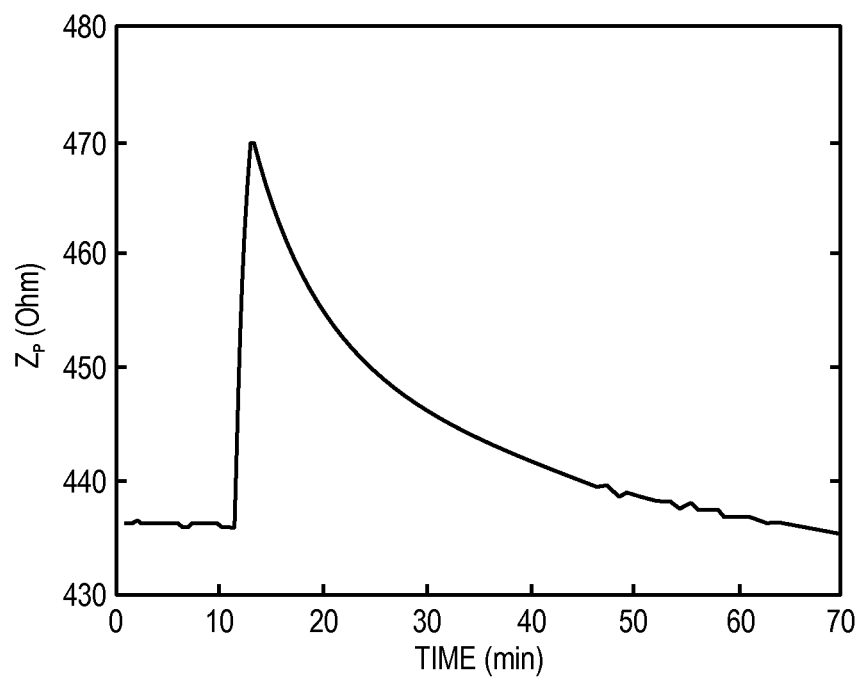
FIG. 5C is a graphical representation of an experimental result obtained with a third sensor, in accordance with embodiments of the present disclosure.

During the experiment, the $ClO_2$ concentration in air was approximately 500 ppm via dilution with dry air and the relative humidity was maintained at approximately 40%. Sensors were exposed to the $ClO_2$ for a time period of approximately thirty seconds. The resultant responses of three experiments are shown in FIG. 5. Each of the three experiments was conducted using a different sensor with the same manually deposited sensing film. FIGS. 5A, 5B, and 5C were produced using three different sensors, each with a passive RFID platform transducer and 0.8% Pt doped Indium oxide as the sensing material. As can be appreciated by FIG. 5, each experiment produced similar results with only slight variations. Importantly, each sensor responded promptly to analyte exposure and then returned to the original, pre-exposure, level. Therefore, FIG. 5 illustrates the reversible feature of each of the three sensors.

Figure 6:
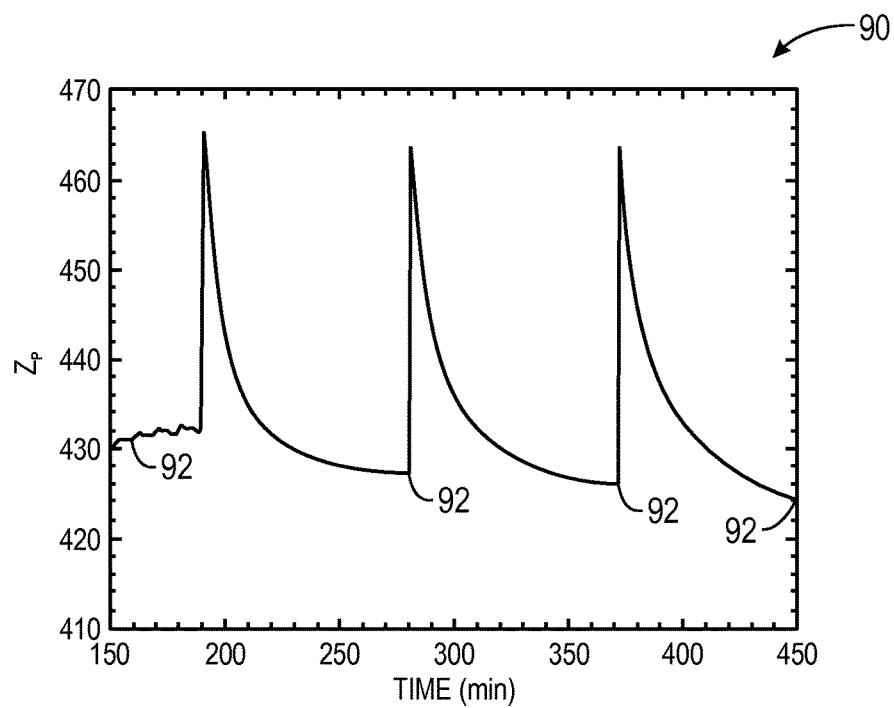
FIG. 6 is a graphical representation of the baseline stability, or reversibility, of a sensor response, in accordance with embodiments of the present disclosure.

FIG. 6 similarly conveys a graphical representation 90 of the results from an experiment utilizing an embodiment of the invention. A sensor with a passive RFID platform transducer and a sensing material with 0.8% Pt doped Indium oxide was utilized to produce the results in FIG. 6.

Additionally, the experimental setup used to produce the results in FIG. 6 is illustrated in FIG. 4. The flow rate of analyte was 400 cc/min such that the sensor was exposed to a 500 ppm concentration of $ClO_2$ for 30 seconds, followed by exposure to air with 40% humidity. The interval between exposures to $ClO_2$ was 60 minutes.

FIG. 6 specifically shows the baseline stability, or reversibility, of the sensor response to three repeated measurements. The sensor response in FIG. 6 is reversible because it returned to its original, pre-exposure level 92 upon removal of the analyte in each of the three measurements. In addition, the repeated measurements were performed to determine the sensor stability and detection limit. The detection limit is a calculated value representing the lowest concentration of an analyte that the sensor can detect. The detection limit (DL) was calculated to be 8 ppm of $ClO_2$, and it was calculated at a signal to noise ratio of 3 using the measured values of $\Delta Z_p = 33.4$ ohm, Std $Z_p = 0.18$ ohm to be DL=8.1 ppm.

Figure 7:
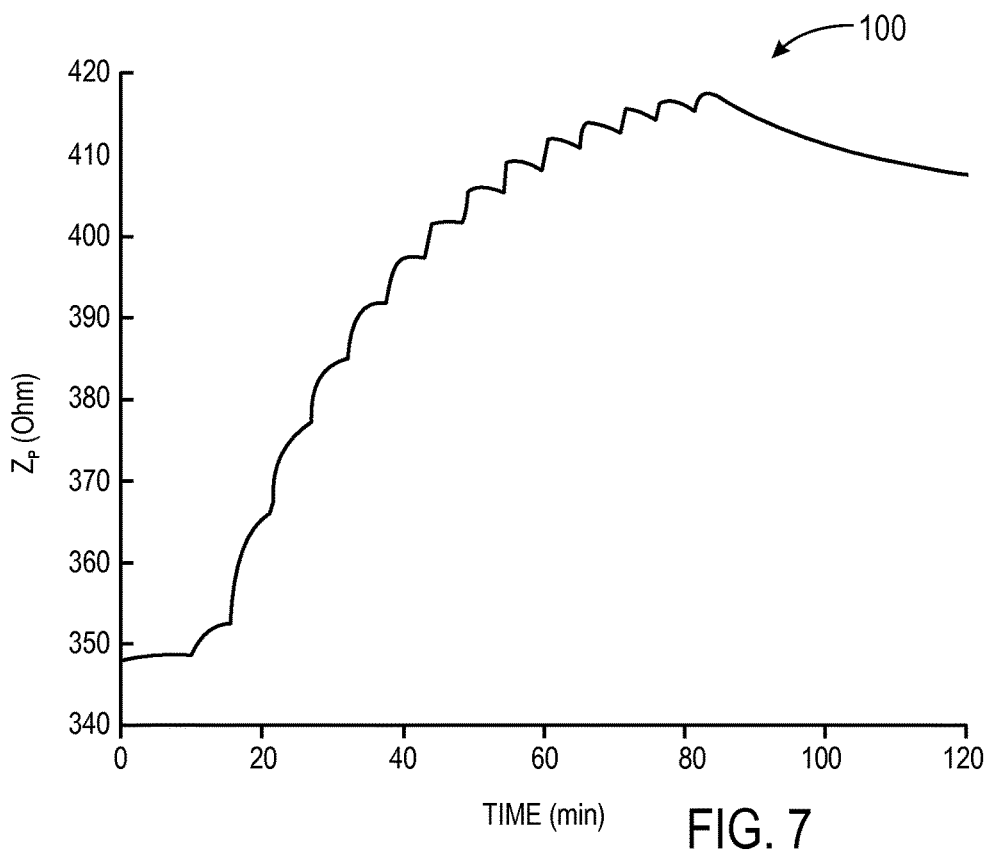
FIG. 7 is a graphical representation of a sensor response to increasing concentration levels of an analyte, in accordance with embodiments of the present disclosure.

FIG. 7 illustrates a graphical representation of the results from testing an embodiment of the invention. Specifically, FIG. 7 shows the response of a sensor responding to increasing $ClO_2$ levels. During the experiment, the $ClO_2$ concentration in air was between 30-300 ppm with a 20 ppm interval, which was controlled using dilution with dry air. The relative humidity was approximately 40%. The resolution of $ClO_2$ concentration that the sensor detected was optimized based on the formulation ratio of the semiconducting mixed metal oxide and polymer matrix. As a non-limiting example, to achieve a resolution of 20 ppm the sensing material formulation included a base metal oxide, namely Indium Tin oxide (ITO) and a polymer matrix, namely polyvinylidene fluoride (PVDF) with the formulation containing 3 mg of the semiconducting metal oxide and 67% of the polymer binder in 1-Methyl-2-Pyrrolidinone (NMP) solvent. The resultant response of three experiments with an exposure time of thirty seconds and equilibrium time of 5 minutes for each level concentration are shown, and the corresponding calibration chart was plotted from these numbers. FIG. 7 illustrates that after the last exposure to $ClO_2$ the sensor signal slowly returns to its original baseline.

Figure 8:
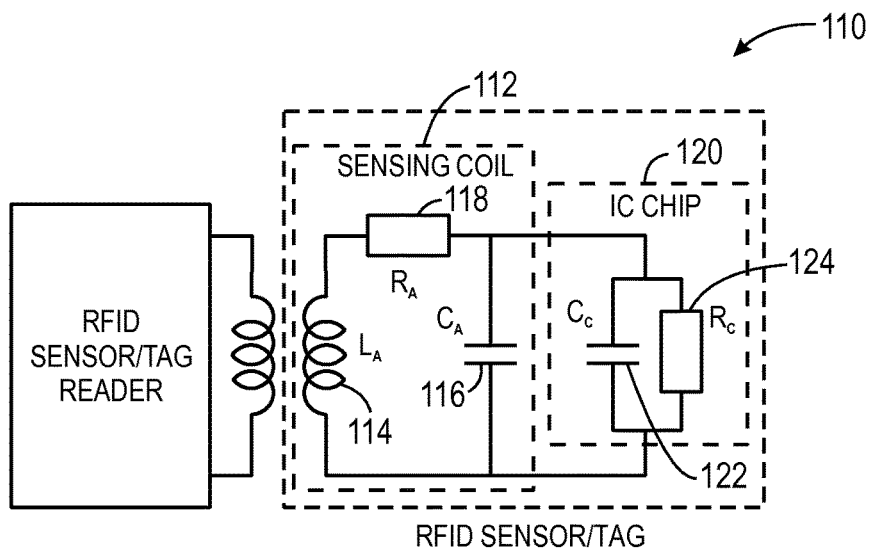
FIG. 8 is a schematic representation of an equivalent circuit diagram of a sensor with an IC memory chip and a sensing coil, in accordance with embodiments of the present disclosure.

FIG. 8 shows an embodiment of an equivalent circuit of a multivariable sensor 110 with an RFID platform transducer. The sensor 110 has a sensing coil 112 with inductance $L_A$ 114, capacitance $C_A$ 116, and resistance $R_A$ 118; a sensing antenna; a sensing material; and an IC chip 120 with capacitance $C_C$ 122 and resistance $R_C$ 124. The complex permittivity of the sensing material applied to the sensing region as shown in either FIG. 1A or 1B is described as $\in'_r - j\in''_r$, where the real part $\in'_r$ corresponds to the energy storage capacity of the sensing material and the imaginary part $\in''_r$ is directly proportional to conductivity σ. Therefore, the sensing material exhibits a capacitance response through the real part $\in'_r$ of the complex permittivity, and the sensing material exhibits a resistance response through the imaginary part $\in''_r$ of the complex permittivity. The real part of the complex permittivity corresponds to the energy storage capability of the sensing material, which is proportionate to the capacitance of the sensing material. Further, because the imaginary part of the complex permittivity is proportional to conductivity it is inversely proportional to resistance because conductivity and resistance are inversely related.

Thus, by measuring the complex permittivity of the sensing material, the sensing material's response to both a change in resistance and a change in capacitance can be measured.

The sensor also has the ability to obtain accurate measurements at ambient temperatures even though fluctuations in temperature may occur. Variations in ambient temperature produce independent effects on the different components of the equivalent circuit in FIG. 8. However, these independent effects are correlated with the spectral features of the resonance impedance spectra and are resolved by the multivariable response of the sensor.

Examples of designs of multivariable sensing materials for embodiments of the present disclosure are presented in FIG. 9. To produce a multivariable response, materials can have a vapor-inert core or a vapor-active core, which may include a first component 130. The first component 130 is surrounded with a complete-coverage layer, shell, or matrix, which may include a second component 132, (e.g., as illustrated in FIG. 9A) or an incomplete-coverage layer, shell, or matrix (e.g., as illustrated in FIGS. 9B and 9C). In certain embodiments, the layer, shell, or matrix may include the second component 132 and a third component 134 as shown in FIG. 9C. In other embodiments, the layer, shell, or matrix may include more than two components. The number of components in the multivariable sensing material may be between 1 and 20, where each component performs a different function in the sensing film. The first component 130 of the multivariable sensing material can include nanoparticles, microparticles, nanowires, and nanotubes. The material of the first component 130 may be a conducting material, a semiconducting material, or a non-conducting material. The shape of the first component 130 can be controlled or random. Additionally, dimensions of the first component 130 may be unaffected by exposure to a vapor or the first component 130 dimensions may be affected by such exposure. If affected by the exposure to a vapor, the first component 130 dimensions may shrink or swell, or exhibit a change in a dielectric property, an electric property, and/or an optical property.

The layer, shell, or matrix can be a conformal layer, a monolayer, or a non-conformal layer, that includes at least one nanoparticle, microparticle, nanowire, or a nanotube. Additionally, a filler matrix may fill a void between the first component 130 and the layer, shell, or matrix. The second component 132 and/or the third component 134 may be a conducting material, a semiconducting material, or a non-conducting material. The shape of the layer, shell or matrix attributes can be controlled or random. Dimensions of the layer, shell, or matrix may be unaffected by exposure to a vapor or the dimensions of the layer, shell, or matrix may be affected by vapors. If affected by the exposure to a vapor, the layer shell, or matrix dimensions may shrink or swell, or exhibit a change in a dielectric property, an electric property, and/or an optical property.

In certain embodiments, the multivariable sensing material may include a hybrid structure such that more than two materials (e.g., metal oxides, metal oxide frameworks, organic ligand-capped nanoparticles, inorganic ligand-capped nanoparticles, polymeric ligand-capped nanoparticles, or mixed metal oxides) are connected by a strong physical bond or interaction. Hybrid multivariable sensing materials may have micro- or nano-structural features such as physical interactions between conducting noble metals, conducting organic polymeric materials, and functionalized nanomaterials.

FIG. 10 is a graphical representation 140 of experimental results obtained with one resonant sensor upon exposure of the sensor to three different vapors. The experimental setup 70 used to produce the results in FIG. 10 is illustrated in FIG. 4. FIG. 10 depicts a response of the sensor 76 to several vapors (e.g., ammonia, methanol, and chlorine), in which the sensor 76 has a $WO_3$—ZnO mixed oxide sensing material. The experiment was conducted at 400° C. and the sensor 76 was operated in resonant mode to measure resonant spectra. The tested vapors were chlorine at concentrations of 10, 20, and 40 ppm, methanol at concentrations of 15, 30, and 60 ppm, and ammonia at concentrations of 20, 40, and 80 ppm. The sensor 76 response was measured as real and imaginary portions of the resonance impedance. FIG. 10 shows a scores plot 140 upon principal components analysis of several responses from the sensor 76. This plot 140 shows that the sensor 76 could distinguish between the three different vapors to which the sensor 76 was exposed.

FIG. 11 is a graphical representation of experimental results 150 obtained with another resonant sensor upon exposure of the sensor to three different vapors. The experimental setup 70 used to produce the results in FIG. 11 is illustrated in FIG. 4. FIG. 11 depicts a response of the sensor 76 to several vapors (e.g., ammonia, methanol, and methyl salicylate (MeS)), in which the sensor 76 has a Pt doped $In_2O_3$ metal oxide sensing material. The experiment was conducted at 300° C. and the sensor 76 was operated in resonant mode to measure resonant spectra. The tested vapors were ammonia at concentrations of 20, 40, and 60 ppm, methyl salicylate at concentrations of 15, 30, and 45 ppm, and methanol at concentrations of 100, 200, and 300 ppm. The sensor 76 response was measured as real and imaginary portions of the resonance impedance. FIG. 11 shows a scores plot 150 upon principal components analysis of several responses from the sensor 76. This plot 150 shows that the sensor 76 could distinguish between the three different vapors to which the sensor 76 was exposed.

FIG. 12 is a graphical representation 160 of experimental results obtained with one resonant sensor upon exposure of the sensor to five different vapors. The experimental setup 70 used to produce the results in FIG. 12 is illustrated in FIG. 4. FIG. 12 depicts a response of the sensor 76 to several vapors (e.g., hydrogen peroxide, ethanolamine, water, chlorine dioxide, and ammonia), in which the sensor 76 has a $SnO_2$—Pd composite sensing material. The experiment was conducted at 300° C. and the sensor 76 was operated in resonant mode to measure resonant spectra. The tested vapors were hydrogen peroxide, ethanolamine, water, chlorine dioxide, ammonia, and water. The concentrations of the tested vapors were ⅛, ¼ and ½ $P/P_o$, where P is vapor partial pressure and $P_o$ is the saturated vapor pressure. Sensor 76 response was measured as real and imaginary portions of the resonance impedance. FIG. 12 shows a scores plot 160 upon principal components analysis of several responses from the sensor 76. This plot 160 shows that the sensor 76 with $SnO_2$—Pd as the sensing material could distinguish between the five different vapors to which the sensor 76 was exposed.

In certain embodiments, an $SnO_2$—Pd composite is synthesized by dissolving sodium stannate trihydrate (e.g., 2 g) in DI water (e.g., 15 mL). D-glucose monohydrate (e.g., 1 g) is added to the sodium stannate trihydrate and water mixture and stirred overnight at 60° C. in an oil bath. The white precipitate that forms is collected by centrifuge separation, and is followed by washing with DI water. The collected nanoparticle is dried by lyophilization overnight. About 300 mg of $SnO_2$ is dispersed in 30 mL of water. To this mixture, sodium tetrachloropalladate (e.g., 7 mg) is added, followed by an addition of sodium borohydride (e.g., 8 mg). This procedure produces a final noncomposite structure with a Pd ratio of 0.8%. This reaction mixture may be stirred overnight and purified of the final nanoparticles using centrifuge washing.

FIG. 13 is a graphical representation 170 of experimental results obtained with another resonant sensor upon exposure of the sensor to five different vapors. The experimental setup 70 used to produce the results in FIG. 13 is illustrated in FIG. 4. FIG. 13 depicts a response of the sensor 76 to several vapors (e.g., hydrogen peroxide, ethanolamine, water, chlorine dioxide, and ammonia), in which the sensor 76 has only $SnO_2$ as a composite sensing material. The experiment was conducted at 300° C. and the sensor 76 was operated in resonant mode to measure resonant spectra. The tested vapors were hydrogen peroxide, ethanolamine, water, chlorine dioxide, ammonia, and water. The concentrations of the tested vapors were ⅛, ¼ and ½ $P/P_o$, where P is vapor partial pressure and $P_o$ is the saturated vapor pressure. Sensor 76 response was measured as real and imaginary portions of the resonance impedance. FIG. 13 shows a scores plot 170 upon principal components analysis of several responses from the sensor 76. This plot 170 shows that the sensor 76 with $SnO_2$ as the sensing material could distinguish between the five different vapors to which the sensor 76 was exposed.

FIG. 14 is a graphical representation 180 of experimental results obtained with one resonant sensor upon exposure to three different vapors. The experimental setup 70 used to produce the results in FIG. 14 is illustrated in FIG. 4. FIG. 14 depicts a response of the sensor 76 to several vapors (e.g., ethanol, methyl ethyl ketone, and water), in which the sensor 76 has a silver ink having silver nanoparticles as a sensing material. The silver nanoparticles were about 20 nm in diameter and had a shell of polyvinylpyrrolidone polymer. The experiment was conducted at ambient room temperature (e.g., approximately 20° C.) and the sensor 76 was operated in resonant mode to measure resonant spectra. The tested vapors were ethanol, methyl ethyl ketone, and water. The concentrations of the tested vapors were ⅛, ¼ and ½ $P/P_o$. Sensor 76 response was measured as real and imaginary portions of the resonance impedance. FIG. 14 shows a scores plot 180 upon principal components analysis of several responses from the sensor 76. This plot 180 shows that the sensor 76 with silver nanoparticles having a polyvinylpyrrolidone shell sensing material could distinguish between the three different vapors to which the sensor 76 was exposed.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A sensor configured to detect a gaseous agent comprising:
   a transducer, wherein the transducer comprises an electrical resonant circuit that forms an antenna; and
   a sensing material disposed at least on the portion of the transducer, wherein the sensing material comprises a tunable polymer additive configured to enable the sensing material to achieve an improved sensing performance, and wherein the sensing material is configured to simultaneously exhibit a capacitance response and a resistance response when exposed to a gaseous agent.

2. The sensor of claim 1, wherein the gaseous agent is a sterilization agent, a fumigation agent, or a decontamination agent.

3. The sensor of claim 1, wherein the sensing material has a reversible response when exposed to the gaseous agent.

4. The sensor of claim 1, wherein the sensing material is configured to measure a concentration of the gaseous agent as a dosimeter.

5. The sensor of claim 1, wherein the sensing material comprises metal nanoparticles coated at least in part with an organic layer.

6. The sensor of claim 1, wherein the sensing material comprises a semiconducting metal oxide and a noble metal catalyst deposited on the semiconducting metal oxide.

7. The sensor of claim 6, wherein the noble metal catalyst is any one of the following: platinum, palladium, gold, silver, aluminum, copper, iron, nickel, ruthenium, or any combination thereof, and wherein the semiconducting metal oxide is any one of the following: $In_2O_3$, $ZnO$, $WO_3$, $SnO_2$, $TiO_2$, $Fe_2O_3$, $Ga_2O_3$ and $Sb_2O_3$ or any other semiconducting metal oxide, or a combination of one or more metals including $In_2O_3$ with $SnO_2$, $In_2O_3$ with $ZnO$, $SnO_2$ with $ZnO$, or any other combination of metals.

8. The sensor of claim 6, wherein the noble metal catalyst is deposited on the semiconducting metal oxide using wetness impregnation or in-situ synthesis.

9. The sensor of claim 6, wherein the weight percentage of noble metal catalyst to semiconducting metal oxide is in the range of 0.01% to 1%.

10. The sensor of claim 1, wherein the sensor is configured to operate at an ambient temperature.

11. The sensor of claim 10, wherein the ambient temperature is between −40 degrees Centigrade to 1000 degrees Centigrade.

12. The sensor of claim 1, wherein the transducer is a passive RFID platform transducer, an inductor-capacitor-resistor (LCR) resonator, a thickness shear mode resonator, an interdigital electrode structure, or an electrode structure.

13. The sensor of claim 1, wherein the sensing material is disposed on a complementary sensing region of the sensor.

14. A sensor configured to detect a gaseous agent, the sensor comprising:
   a transducer, wherein the transducer comprises an antenna;
   a sensing material disposed on the transducer, wherein the sensing material comprises a semiconducting metal oxide, a noble metal catalyst deposited on the semiconducting metal oxide, and a tunable polymer additive configured to enable the sensing material to achieve an improved sensing performance; and
   wherein the antenna is configured to emit an electric field to probe a response of the sensing material when exposed to a gaseous agent.

15. The sensor of claim 14, wherein the semiconducting metal oxide is a semiconducting mixed metal oxide.

16. The sensor of claim 14, wherein the sensing material comprises between 1% and 80% of the tunable polymer additive.

17. The sensor of claim 14, wherein the response of the sensing material is both a change in a capacitance and a change in a resistance.

18. The sensor of claim 14, wherein the sensing material is disposed on a complementary sensing region of the sensor.

19. A method for preparing a sensor configured to detect a gaseous agent comprising:
   assembling a transducer by disposing an antenna on a substrate;

doping a noble metal catalyst to a semiconducting metal oxide to form a metal oxide powder;

mixing the metal oxide powder with an aqueous solution of a polymer matrix to form a stable metal oxide suspension;

depositing the metal oxide suspension on the transducer; and drying the metal oxide suspension to form a sensing material, wherein the polymer matrix is configured to enable the sensing material to achieve an improved sensing performance.

20. The method of claim 19, wherein the noble metal catalyst is any one of the following: platinum, palladium, gold, silver, aluminum, copper, iron, nickel, ruthenium, or any combination thereof.

21. The method of claim 19, wherein the semiconducting metal oxide is any one of the following: $In_2O_3$, ZnO, $WO_3$, $SnO_2$, $TiO_2$, $Fe_2O_3$, $Ga_2O_3$ and $Sb_2O_3$ or any other semiconducting metal oxide, or a combination of one or more metals including $In_2O_3$ with $SnO_2$, $In_2O_3$ with ZnO, $SnO_2$ with ZnO, or any other combination of metals.

22. The method of claim 19, wherein the polymer matrix is formed by dissolving a polymer additive in water, ethanol, isopropanol, hexane, toluene, 1-Methyl-2-Pyrrolidinone, or any combination thereof.

23. The method of claim 19, wherein the polymer matrix is any of the following: polyvinlyldene fluoride (PVDF), polyvinyl alcohol (PVO), polyacrylic acid (PAA), chloro metal acid, or any combination thereof.

24. The method of claim 18, wherein disposing the antenna on the transducer is performed using printing.

25. A method for detecting a concentration of a gaseous agent comprising:

exposing a sensing material to a gaseous agent, wherein the sensing material comprises a first component, a second component, and a tunable polymer additive, and wherein the first component, the second component, and the tunable polymer additive are deposited on a surface of a sensing coil, wherein the tunable polymer additive is configured to enable the sensing material to achieve an improved sensing performance;

oxidizing or reducing the first component and/or the second component;

measuring a capacitance response and a resistance response of the sensing material over a frequency range; and conducting analysis on the capacitance response and the resistance response of the sensing material to detect a concentration of the gaseous agent.

26. The method of claim 25, wherein the sensing material comprises metal nanoparticles coated at least in part with an organic layer.

27. The method of claim 25, wherein the analysis is univariate or multivariate.

28. The method of claim 25, wherein the first component is a semiconducting metal oxide and the second component is a noble metal catalyst, and wherein the noble metal catalyst is deposited on the surface of the semiconducting metal oxide.

29. The method of claim 25, wherein the analysis facilitates for self-correction against fluctuations in ambient temperature.

30. The method of claim 25, wherein the sensing material has a reversible response to the gaseous agent.

31. The sensor of claim 1, wherein a weight percent of the tunable polymer additive in the sensing material is between 60% and 80%.

32. The sensor of claim 1, wherein a weight percent of the tunable polymer additive in the sensing material is approximately 76%.

33. The sensor of claim 1, wherein the improved sensing performance is to simultaneously exhibit the capacitance response and the resistance response when exposed to a gaseous agent at a concentration of about 30 parts per million (ppm) and 300 ppm without exhibiting a response saturation at 300 ppm.

34. The sensor of claim 14, wherein a weight percent of the tunable polymer additive in the sensing material is between 60% and 80%.

35. The sensor of claim 14, wherein a weight percent of the tunable polymer additive in the sensing material is approximately 76%.

36. The sensor of claim 14, wherein the improved sensing performance is to exhibit a response when exposed to a gaseous agent at a concentration of about 30 parts per million (ppm) and 300 ppm without exhibiting a response saturation at 300 ppm.

* * * * *